United States Patent [19]
Oikawa

[11] Patent Number: 6,104,776
[45] Date of Patent: Aug. 15, 2000

[54] NONDESTRUCTIVE TEST APPARATUS

[75] Inventor: Shiro Oikawa, Shiga, Japan

[73] Assignee: Shimadzu Corporation, Kyoto, Japan

[21] Appl. No.: 09/123,360

[22] Filed: Jul. 28, 1998

[30] Foreign Application Priority Data

Jul. 31, 1997 [JP] Japan .................................... 9-221084

[51] Int. Cl.[7] .............................. A61B 6/00; G01N 23/04
[52] U.S. Cl. .................................. 378/22; 378/4; 378/10; 378/19; 378/20; 378/21; 378/57
[58] Field of Search .................................. 378/22, 21, 4, 378/57, 10, 19, 20

[56] References Cited

U.S. PATENT DOCUMENTS 5,012,498  4/1991  Cuzin et al. ............................... 378/22
5,717,732  2/1998  Tam ............................................ 378/4

Primary Examiner—Samuel A. Turner
Assistant Examiner—Armando Rodriguez
Attorney, Agent, or Firm—Kanesaka & Takeuchi

[57] ABSTRACT

A nondestructive test apparatus for testing a work is formed of a fixed radiation generating device; a rotatable work holding device situated near the radiation generating device; and a rotatable radiation image taking device situated near the work holding device at a side opposite to the radiation generating device. The radiation image taking device rotates or swings in accordance with rotation or swinging of the work holding device at a same angle thereto. The radiation image taking device receives and accumulates images of the work held on the work holding device and radiated by the radiation generating device while the work is being rotated or swung. It is possible to quickly obtain a sectional image with the relatively simple and compact structure. The test or inspection efficiency can be improved.

8 Claims, 6 Drawing Sheets

NONDESTRUCTIVE TEST APPARATUS

BACKGROUND OF THE INVENTION AND RELATED ART STATEMENT

The present invention relates to a nondestructive test apparatus by radiation, such as X-rays, which is suitable to test or inspect a connecting portion of an electronic part mounted substrate, contact surfaces of different materials for complex materials and so on.

Nondestructive test apparatuses using X-rays have long history. When the nondestructive test apparatuses are classified technologically, the test apparatuses are classified into a simple X-ray filming having, as a sensor, a X-ray film, X-ray image intensifier or imaging plate, and a sectional filming or sectional image taken by X-ray CT. Basically, the technology has been developed and matured as a medical diagnostic apparatus.

As an apparatus developed from the simple X-ray filming, a two-dimensional transmission image, which is called a sectional filming or sectional photograph hereinafter, has been obtained, wherein a X-ray source and a sensor are scanned with a specific relationship around a work or body to be tested to thereby emphasize an image at a predetermined section. This is made by operating or scanning the X-ray source and the sensor at different planes or sections such that portions of the work on a predetermined section are projected on the same position of the sensor. In this method, the transmission image of the portions of the work on the specific section appears clearly on the sensor, but other portions of the work located on the planes or sections other than the predetermined section are projected on the different locations of the sensor by the movements of the X-ray source and the sensor to thereby allow the image to appear unclearly on the face or plane of the sensor. The resolution in the direction of the depth is not clear like a sectional image by the X-ray CT, but this method is advantageous in easily and simply obtaining the two-dimensional transmission image separated in the direction of the depth.

However, in the conventional sectional image photographing apparatus, the X-ray source and the sensor are moved on the respective planes parallel to the work to be tested. Especially, since an X-ray tube used as the X-ray source is very heavy, the X-ray tube can not be moved fast, so that the test can not be performed efficiently. Also, since the X-ray source and the sensor are moved on the respective planes parallel to each other, the apparatus becomes large. Thus, it is difficult to form the apparatus compact as a whole.

The present invention has been made in view of the above, and an object of the invention is to provide a nondestructive test apparatus in the sectional image photographing type, which can be operated or scanned fast for testing efficiently.

Another object of the invention is to provide a nondestructive test apparatus as stated above, which can be formed relatively compact as a whole.

SUMMARY OF THE INVENTION

In order to attain the above objects, a nondestructive test apparatus of the first aspect of the invention comprises fixed radiation generating means, rotatable work holding means, and rotatable radiation image taking or photographing means. The radiation image taking means rotates in accordance with and at an angle same as that of the work holding means, and accumulates images of the work held on the work holding means and radiated by the radiation generating means while the work is being rotated.

In the second aspect of the invention, in addition to the above structure as stated in the first aspect, the nondestructive test apparatus further includes image processing means attached to the radiation image taking means. The image processing means suppresses low frequency components relating to the images in the rotational directions, i.e. the images not in the predetermined section, in the accumulated image data obtained by the radiation image taking means.

In the third aspect of the invention, in addition to the image processing means, the nondestructive test apparatus further includes means for smoothly changing radiation intensity received at the radiation image taking means according to the rotational angle of the radiation image taking means.

The work to be tested is held by the work holding means and rotated. In association with the rotation, the radiation image taking means rotates simultaneously for the same angle. Therefore, when the work with a predetermined section is rotated, an image receiving face or plane of the radiation image taking means rotates parallel to the predetermined section while keeping the parallel condition. Thus, the transmission image of the work located on the predetermined section is only projected onto the same position of the receiving face or plane of the radiation image taking means. Since the images are accumulated during the rotation, the two-dimensional transmission image on the predetermined section can be clearly obtained. On the other hand, the projected locations of the transmission images on the receiving face located other than the predetermined section move along the rotation of the work holding means and the radiation image taking means. Thus, when the images are accumulated during the rotation, the images becomes unclear.

The radiation generating means is generally a very heavy device. However, in the present apparatus, since the radiation generating means is fixed, the weight need not be considered. The work to be tested is a patient in a medical diagnostic apparatus, which can not be rotated, but the work to be tested in the nondestructive test apparatus of the invention is an electronic part mounting plate and so on. Thus, there is no problem in rotating the work. Also, since the work to be treated in the invention is generally very light, it is convenient to rotate the work.

The radiation image taking means is, in case of an X-ray image intensifier, very heavy, but it is not impossible to rotate the same. Further, in the recent technical development, a plane type X-ray face sensor with light weight may be available very soon. If this type of the X-ray face sensor is used, the X-ray face sensor can be rotated easily.

As explained above, the test or inspection is made by fixing the radiation generating means and rotating the work holding means and the radiation image taking means. Thus, it is possible to rotate at the high speed to efficiently test the work. Also, since the work holding means and the radiation image taking means are only rotated, the apparatus can be made mechanically simple and compact.

The image processing is made for suppressing the low frequency components for the rotational direction of the images in the image data obtained from the radiation image taking means. Thus, it is possible to reduce the image intensity of the parts except for the predetermined section, which appears unclearly by spreading the images in the rotational direction. As a result, the image on the predetermined section can be emphasized further.

In addition, if the radiation intensity received in the radiation image taking means is changed smoothly according to the rotational angle thereof, extra high frequency components are not generated. Thus, it is possible to properly reduce the image intensity except for the image on the predetermined section.

DETAILED DESCRIPTION OF PREFERRED EMBODIMENTS

Figure 1:
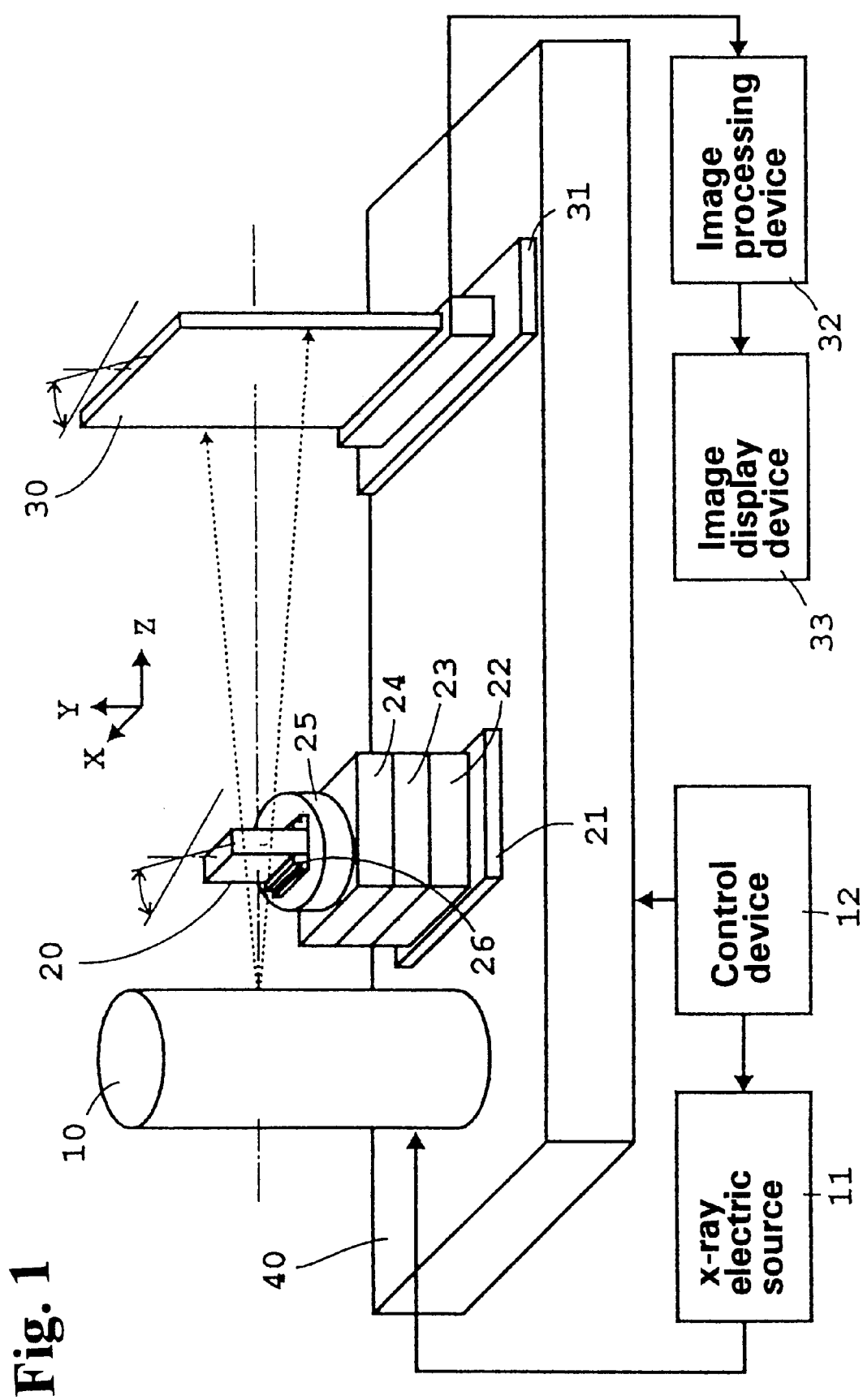
FIG. 1 is a perspective view for schematically illustrating an embodiment of the invention.

The embodiments of the invention will be explained in detail with reference to the drawings. In FIG. 1, an X-ray tube device 10, a test material or work 20 to be tested and an X-ray face sensor 30 in a plane type are mounted on a base 40 along a Z-axis. The X-ray tube device 10 is fixed on the base 40, but the work 20 to be tested and the X-ray face sensor 30 are held on the base 40 such that they can reciprocate or swing within a predetermined angle around a rotational axis parallel to a Y-axis. The swinging angle will be, for example ±45° (90 degrees), in case a direction perpendicular to an X-ray beam, i.e. Z-axis, is defined as 0°.

The work 20 to be tested is attached to a swinging plate 21 through an X-stage 22, Y-stage 23, Z-stage 24 and rotation stage 25. In particular, the work 20 is fixed to the rotation stage 25 by a fixing device 26. The X-stage 22, Y-stage 23 and Z-stage 24 are stages for adjusting the location in the X, Y and Z directions, and the rotation stage 25 is a stage for rotating continuously. The X-ray face sensor 30 is formed of, such as a two-dimensional X-ray sensor in a plane type, wherein electric charge signals accumulated on a light electric conductive layer are read by a two-dimensional TFT array. The X-ray face sensor 30 is fixed onto a swingable plate 31, which is swingable on the base 40.

The swingable plates 21, 31 are actuated by a mechanism installed inside the base 40, which is explained later with reference to FIG. 2. By the mechanism, the work 20 and the X-ray face sensor 30 are synchronized with each other, i.e. the work 20 and the sensor 30 perform reciprocal rotational movements within a predetermined angle while keeping the parallel relationship therebetween. This movement is controlled by a control device 12.

The X-ray tube device 10 is supplied with high tube voltage and tube current from an X-ray electric source, by which X-rays are radiated to the work 20. The X-ray electric source 11 is controlled by the control device 12 so that the tube current is changed according to the angle of the work 20 and the X-ray face sensor 30.

The X-ray face sensor 30 outputs signals of the image accumulated therein for the swinging angle, which are transferred to an image display device 33 through an image processing device 32, so that an image or sectional image at a predetermined section of the work 20 is displayed. The sectional image is located in a plane parallel to an image receiving plane of the X-ray face sensor 30 and passing through a rotational center axis of the work 20.

The base 40 includes a swinging mechanism therein, which keeps the swinging plate 21 for the work and the swinging plate 31 for the X-ray face sensor parallel to each other and allows the both plates to swing together. The mechanism is shown in FIG. 2, as an example.

Figure 2:
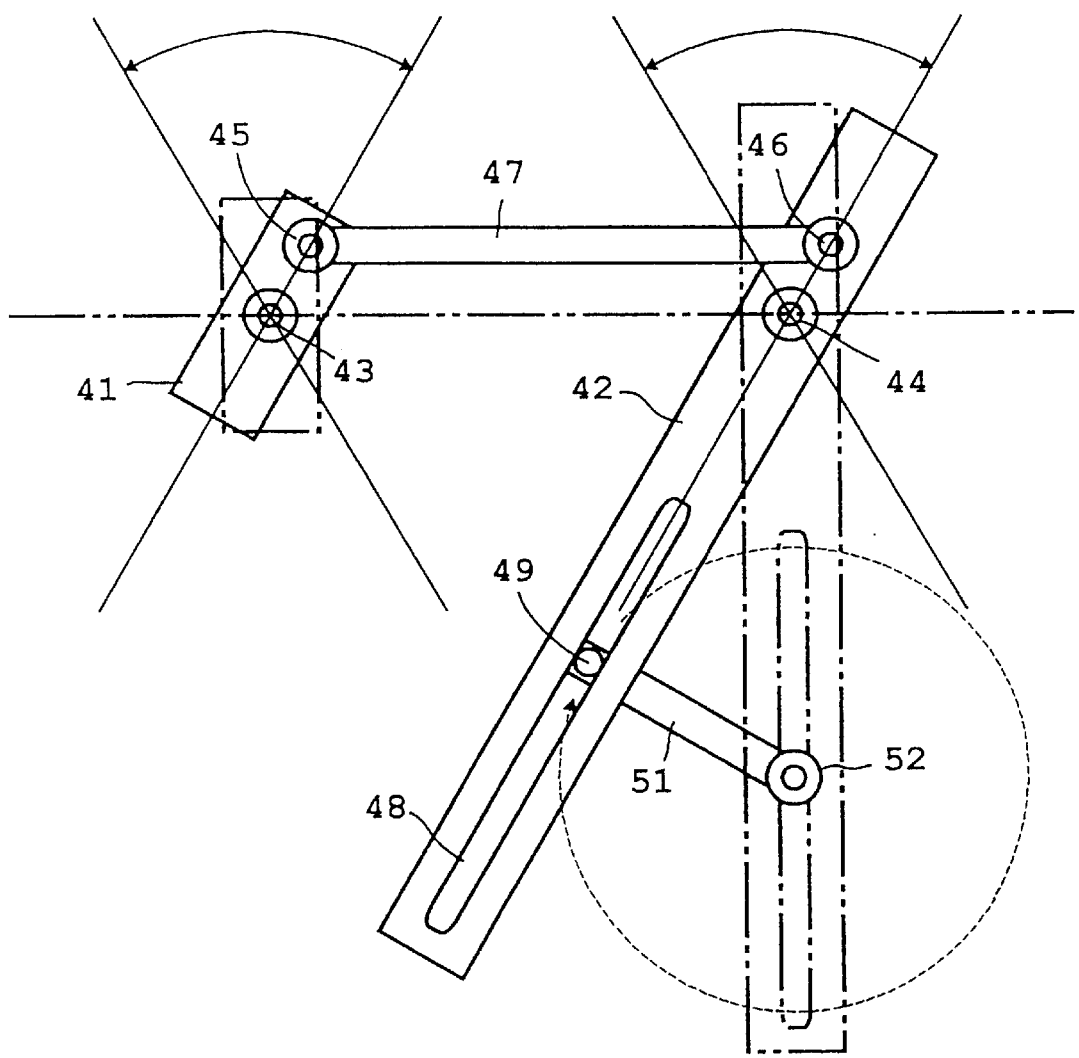
FIG. 2 is a plan view for schematically illustrating an embodiment of a swing-movement mechanism.

In FIG. 2, two swinging levers 41, 42 are supported or held by rotational axes 43, 44, respectively, to thereby allow the levers 41, 42 to rotate around the axes 43, 44. The swinging plates 21, 31 are respectively fixed to the swinging levers 41, 42. Also, the swinging levers 41, 42 are connected together by a link 47 through rotational axes 45, 46. When one of the levers rotates at some angle, the other lever rotates at the same angle, while the levers are kept parallel to each other.

One of the swinging levers, i.e. lever 42, is provided with a sliding groove 48, and a pin 49 engages the sliding groove 48 to slide therein. The pin 49 is provided at a tip of a crank 51 attached to a rotation driving shaft 52. When the crank 51 rotates together with the rotation of the rotation driving shaft 52, the pin 49 rotates while the pin 49 slides in the groove 48. As a result, the swinging lever 42 performs the reciprocal rotational movement in the predetermined angle.

Figure 3:
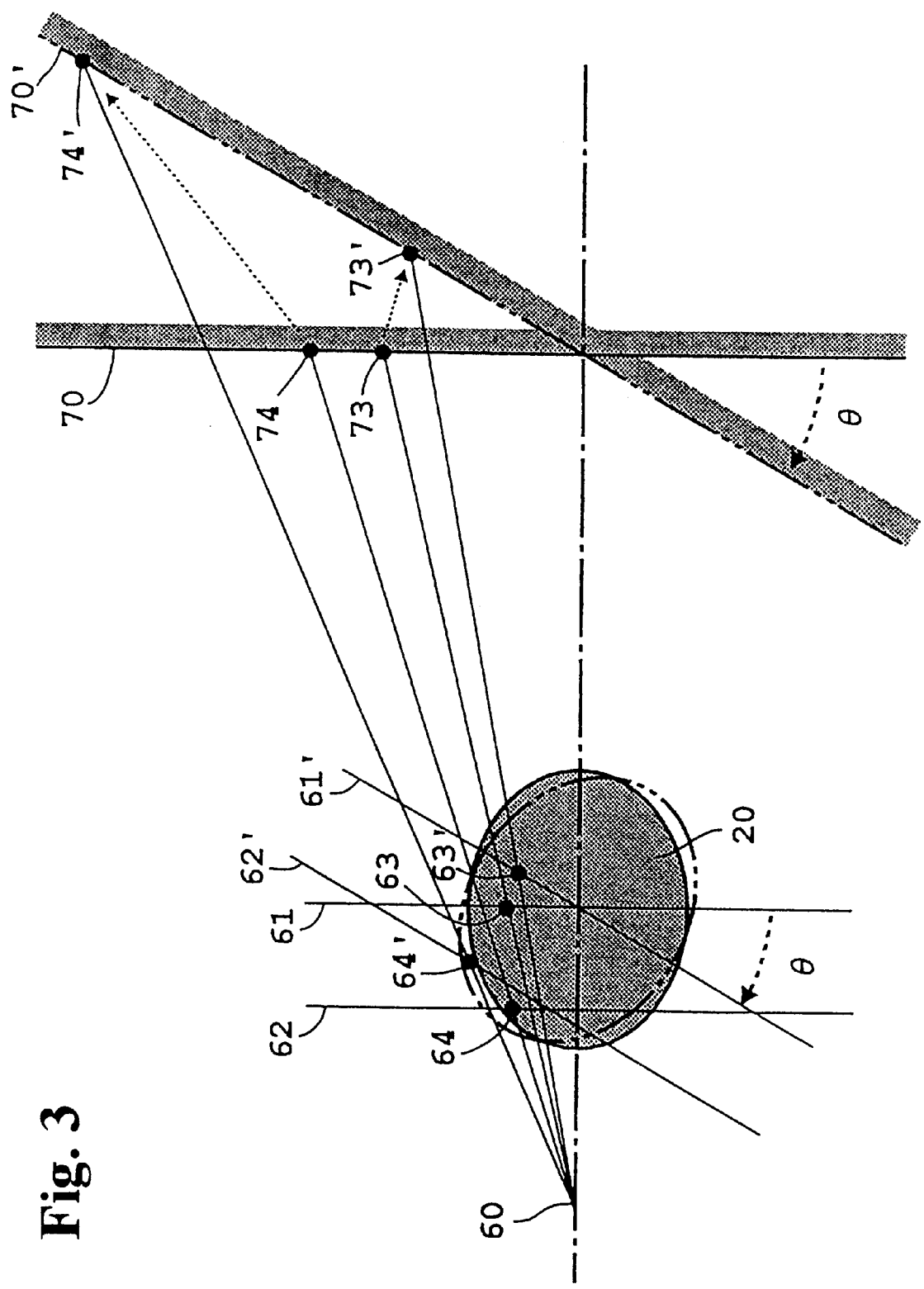
FIG. 3 is an explanatory view for explaining a principle of obtaining a sectional image.

An explanation for the accumulation of the images on the predetermined sectional plane of the work 20 to the X-ray face sensor 30 by the swinging movement is made further in detail with reference to FIG. 3.

In FIG. 3, X-rays projected from an X-ray converging point 60 pass through the work 20 and are received at a receiving face or plane 70 of the X-ray face sensor 30. When the receiving face 70 is oriented perpendicular to the X-ray beam, a portion 63 located on a section 61 perpendicular to the X-ray beam passing through the rotational center axis of the work 20 is projected on the receiving face 70 as an image 73. Also, a portion 64 located on a section 62 perpendicular to the X-ray beam passing through the work 20, which does not pass through the center of the work 20 and is different from the depth, is projected on the receiving face 70 as an image 74.

It is assumed that the work 20 and the receiving face 70 rotate at an angle θ. In this condition, the sections 61, 62 rotate and become sections 61', 62', and the portions 63, 64 rotate to become portions 63', 64'. These portions 63', 64' are projected as images 73', 74' on the rotated receiving face 70'. The section 61 is a plane passing through the rotational center axis, the receiving face or plane 70 also passes through the rotational center axis, and the rotational angles of these planes are the same. Therefore, the projected images of the portion 63, 63' on the sections 61, 61' are located on the same position on the receiving faces 70, 70'. on the other hand, when the angle is changed, the portion on the section 62 different in depth from the section 61 passing through the rotational center axis is projected at a different position on the receiving face 70.

Figure 4:
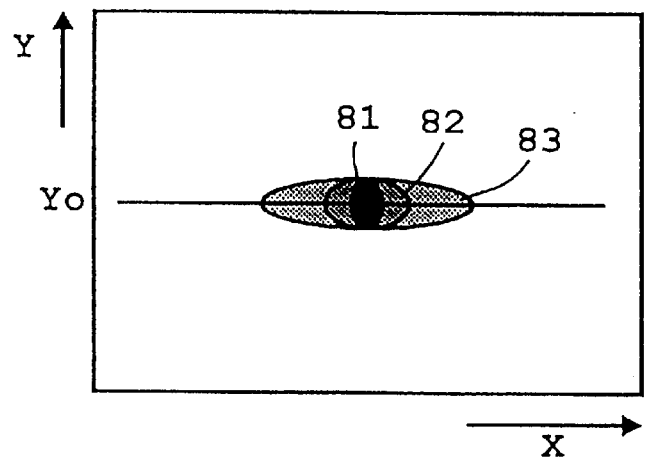
FIG. 4 is a photographed image.

Accordingly, in case the images are accumulated during the swinging movements, the projected images of the part 63 on the section 61 become clear, but the projected images on the sections other than the section 61, e.g. part 64 on the section 62, spread or expand in the direction (X direction) perpendicular to the rotational center axis (parallel to Y axis) to become unclear images. Thus, the images as shown in FIG. 4 are obtained. An image 81 of FIG. 4 is obtained from the portion on the section 61, and an image 82 is obtained from the portion on the section different in depth from the section 61, while the image 83 is obtained from the portion on the section different in depth further from the section 61.

As stated above, the degree of clearness of the images is different according to the position of the section. Since the image on the section passing through the rotational center axis becomes only clear, the sectional image on that plane is obtained. The difference of clearness becomes large as the swinging angle becomes great. Thus, in case the range of the swinging angle is increased, the practical thickness of the sectional image can be made thin. It is possible to set the practical thickness of the sectional image as desired based on the range of the swinging angle.

Figure 5:
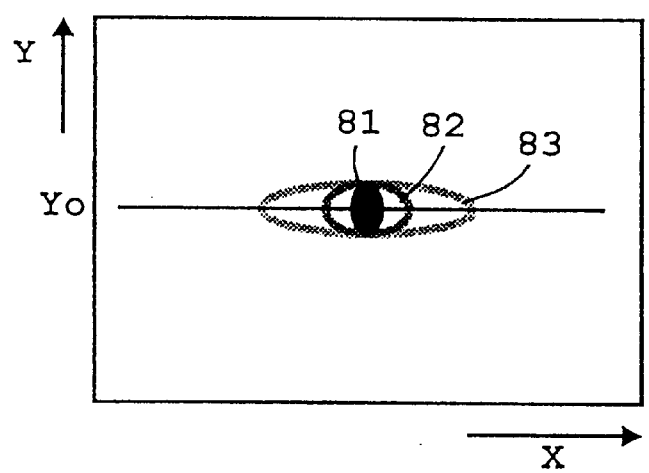
FIG. 5 is a photographed image after image processing for the image shown in FIG. 4.
Figure 6:
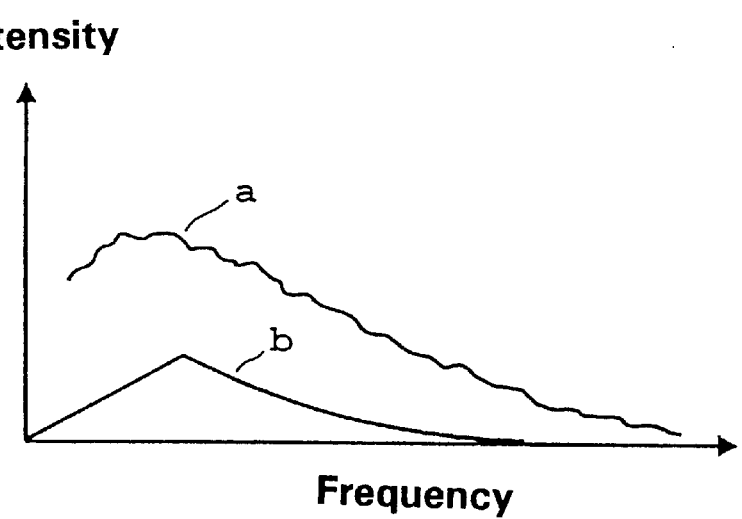
FIG. 6 is a graph for explaining the image processing.

Further, this image is processed by an image processing device, so that as shown in FIG. 5, the image 81 on the section passing through the rotational center axis is emphasized and the images 82, 83 on the other sections are weakened. As this processing, so called "folding calculation" or convolution processing is made. Namely, in case an image intensity distribution on a Yo line is changed by a Fourier transform to obtain frequency components, a curve a in FIG. 6 is obtained, to which a filter function as shown in a curve D is multiplied to thereby suppress the original low frequency components. The value is changed by a reverse Fourier transform for restoration. Since the image processing is simple, it is possible to complete the processing within one second after obtaining the image signal.

In addition, it is preferable to improve the clear image forming ability at the interested area by a general two-dimensional filter processing including the direction, i.e. Y direction, perpendicular to the scanning direction, i.e. X direction.

Here, in order to optimize the uncleanness of the image on the section different from the section passing through the rotational center axis by the folding calculation, it is important that excess high frequency components should not be included in the projected intensity profile in the direction of the swing angle. For this purpose, in case the X-ray electric source 11 is controlled such that the X-ray tube current is changed in response to the swinging angle by the control device 12, and the images are accumulated in the swinging angle between −30° and +30°, the X-ray tube current is changed smoothly and symmetrically relative to 0° as shown in a solid line in FIG. 7($a$). Accordingly, the projected intensity profile in the direction of the swinging angle is changed smoothly, preferably along a Gauss curve, as shown in a solid line in FIG. 7($b$).

Figure 7A:
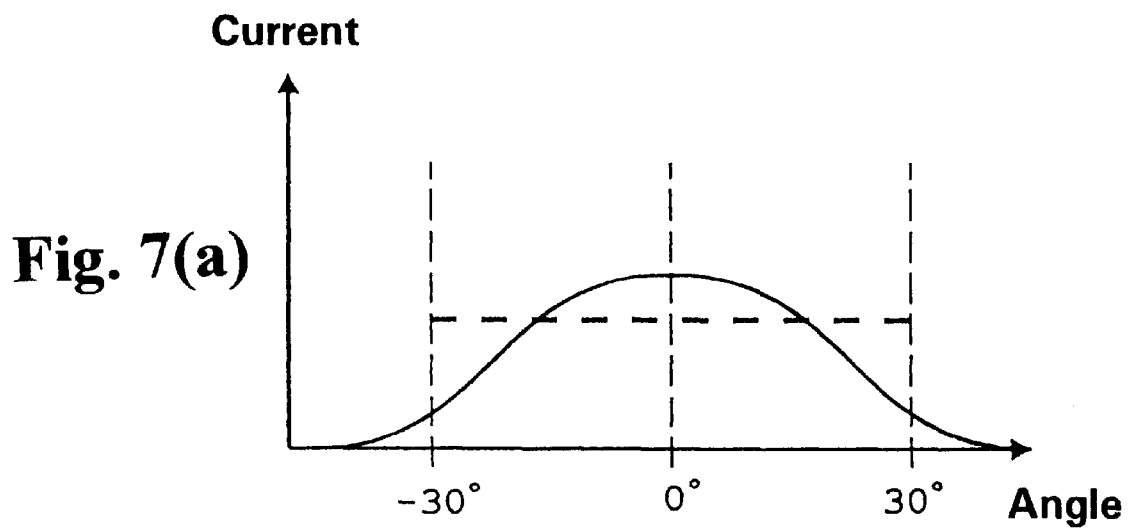
FIGS. 7(a) and 7(b) are graphs for showing current and X-ray projection intensity in accordance with angles.

In case this kind of current control is not made, and the X-ray tube current is supplied simply as shown in a dotted line in FIG. 7($a$) from −30° to +30°, wherein the X-ray tube current is zero outside the angle from −30° to +30°, the projected intensity profile will have a steady value from −30° to +30° as shown in a dotted line in FIG. 7($b$), and the other values are zero. In this case, since high frequency components are largely included, the appropriate image processing can not be performed.

In this example, a micro-focus X-ray tube with a focal point size of several $\mu$m as the X-ray tube, and a plane type X-ray face sensor with a size of several 10 cm as the X-ray sensor, are respectively used. Also, the length from the X-ray focal point to the work 20 is about 20 mm, and the length from the X-ray focal point to the X-ray face sensor 30 is about 1 m. Further, enlarged photograph of 100 times is made for the work 20 with the size of several cm. The swinging is repeated in one second for one round movement. Accordingly, the sectional image can be obtained and displayed within 1 second after the image signal output by processing the images accumulated in one round movement. In case the swinging movement, the image accumulation, and the image processing are made in parallel, it is possible to obtain the sectional images at a high speed, such as one sectional image is obtained in about 1 second sequentially.

As shown in FIG. 1, the work 20 to be tested is placed on the X-stage 22, Y-stage and Z-stage 24 fixed to the swinging plate 21, because the rotation center axis and the section are set as desired by freely moving the work on the X, Y and Z directions. Also, the rotation stage 25 is made to continuously rotate the work 20. The X-ray face sensor 30 may be continuously rotated more that once in the condition that the swinging movement of the X-ray sensor 30 is stopped, and the image signals may be obtained for every angle of the rotation. The image signals are transferred to the image processing device 32 to perform so called CT image reconstruction by the back projection processing and so on to thereby obtain the CT sectional images on the X-Z planes.

Since the CT sectional image or coaxial tomography thus obtained is oriented perpendicular to the above sectional image, the positional relations between them are clear. The interior of the work 20 can be tested or inspected clearly by using both sectional images.

In the above example, the work 20 and the X-ray face sensor 30 are subjected to reciprocal rotational movements or swinging movements at the predetermined angular range. However, the work 20 and the X-ray face sensor 30 may be rotated in one direction continuously, and X-rays may be only projected in a predetermined angular range, e.g. from −30° to +30°, as shown in FIG. 7($a$). During this time, the image may be accumulated in the X-ray face sensor 30. Also, as the mechanism for providing the swinging movement, the link mechanism is used, but other mechanisms, such as gear mechanism, cam mechanism and so on, may be easily employed. It is possible to synchronously rotate or swing the two members directly by using two stepping motors for the two members.

Figure 8:
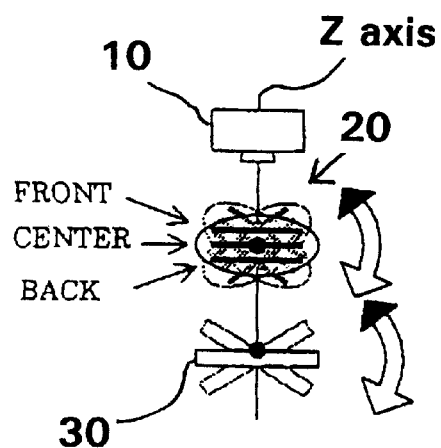
FIG. 8 is an explanatory view for showing a basic oscillation in the embodiment shown in FIG. 1.
Figure 9:
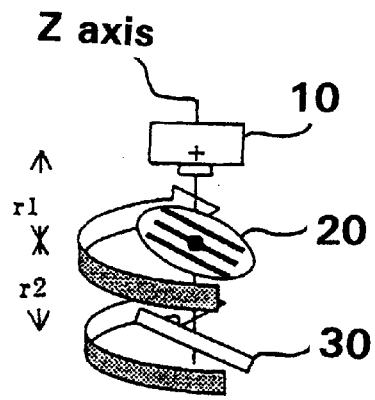
FIG. 9 is an explanatory view for showing a modified operation in another embodiment of the invention.
Figure 10:
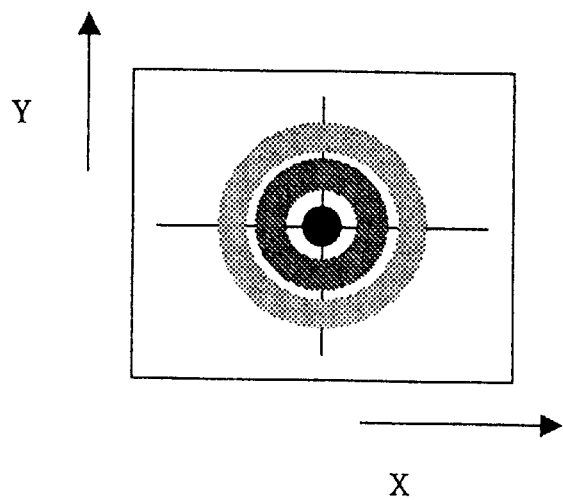
FIG. 10 is a photographed image of the embodiment shown in FIG. 9.
Figure 11:
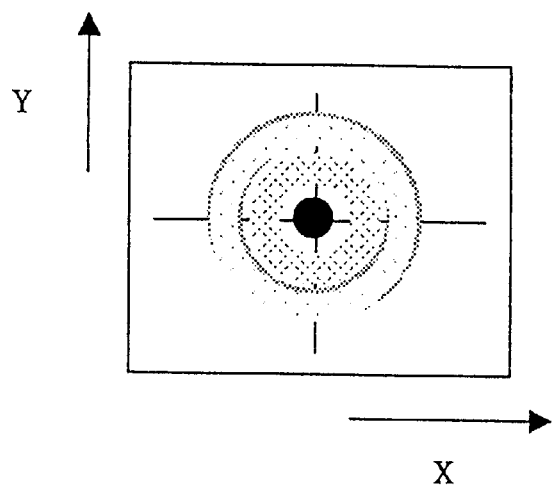
FIG. 11 is a photographed image after image processing for the image shown in FIG. 10.

In the embodiment as shown in FIGS. 4 and 5, the work 20 and the X-ray face sensor 30 are rotated or oscillated along the Y axis, as shown in FIG. 8. However, the work 20 and the X-ray sensor 30 may be inclined relative to the Y axis for a predetermined angle, and in this condition, the work 20 and the X-ray sensor 30 may be rotated around the Z axis for 360 degrees, as shown in FIG. 9. In this case, the image obtained by the X-ray face sensor 30 becomes circular as shown in FIG. 10. The image data as shown in FIG. 10 is processed by filtration and so on, as explained before, so that the image as shown in FIG. 11 is obtained. The black area in FIG. 10 is the section of the work 20, and the accuracy of the image is relatively high.

As the face sensor 30, two-dimensional X-ray face sensor may be sufficient, but it is possible to use an X-ray image intensifier. In this case, since the X-ray image intensifier is relatively heavy, mechanically, it is inferior in size and increasing the swinging speed than those in the plane type X-ray face sensor 30. However, in view of the resolution and sensitivity for the image of the X-ray image intensifier, the immediate response to the signal output thereof, and so on, the X-ray image intensifier may be employed.

Figure 7B:
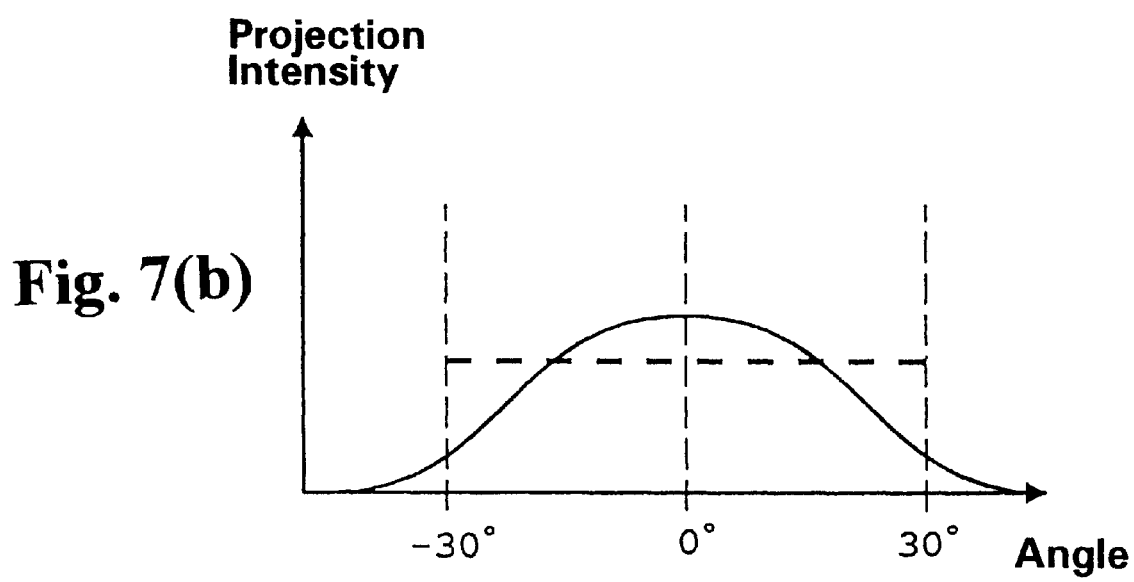

As the structure for smoothly changing the X-ray projection intensity profile as shown in the solid line in FIG. 7(b), X-ray projected from the X-ray tube device 10 may be directly controlled except for controlling the tube current. Namely, a suitable X-ray absorbing material is disposed between the X-ray tube device 10 and the X-ray face sensor 30, and the effective thickness may be changed according to the swinging angle by, for example inclining the X-ray absorbing material.

Further, it is possible to use other radiation sources instead of the X-ray tube device 10. For example, it may be a plasma X-ray source, radioisotope for radiating gamma-ray, electron linac for radiating X-ray, and SOR light source for generating monochromatic X-ray. As stated above, the radiation may be electromagnetic waves with short wavelength other than the X-ray.

As explained above, in accordance with the nondestructive test apparatus of the invention, it is possible to quickly obtain a sectional image with the relatively simple and compact structure. Thus, the test or inspection efficiency can be improved.

What is claimed is:

1. A nondestructive test apparatus for testing a work comprising:

fixed radiation generating means;

rotatable work holding means situated near the radiation generating means; and rotatable radiation image taking means situated near the work holding means at a side opposite to the radiation generating means, said radiation image taking means rotating in accordance with rotation of the work holding means at a same angle thereto, and receiving and accumulating images of the work held on the work holding means and radiated by the radiation generating means while the work is being rotated.

2. A nondestructive test apparatus according to claim 1, further comprising a linking device for connecting the work holding means and the radiation image taking means, said linking device synchronously rotating the work holding means and the radiation image taking means at a same ratio.

3. A nondestructive test apparatus according to claim 2, wherein said linking device reciprocally swings the work holding means and the radiation image taking means at a specific angular range.

4. A nondestructive test apparatus according to claim 2, wherein said work holding means includes a rotation stage for holding the work, and three stages disposed under the rotation stage for adjusting the rotation stage in three-dimensional directions perpendicular to each other.

5. A nondestructive test apparatus according to claim 1, further comprising image processing means attached to the radiation image taking means, said image processing means suppressing low frequency components relating to rotational directions of images in accumulated image data obtained by the radiation image taking means.

6. A nondestructive test apparatus according to claim 5, wherein said image processing means obtains an image on a section passing through a rotational center line of the work.

7. A nondestructive test apparatus according to claim 5, further comprising means for smoothly changing radiation intensity received at the radiation image taking means according to the rotational angle of the radiation image taking means, said radiation intensity changing means being connected to the radiation generating means.

8. A nondestructive test apparatus according to claim 7, wherein said radiation intensity changing means provides current to the radiation generating means according to a rotational angle of the work.

* * * * *